United States Patent
Behler

(10) Patent No.: US 10,125,215 B2
(45) Date of Patent: Nov. 13, 2018

(54) ESTERS OF OLIGO-HYDROXYCARBOXYLIC ACIDS AND USE THEREOF

(71) Applicant: BASF SE, Ludwigshafen (DE)

(72) Inventor: Ansgar Behler, Bottrop (DE)

(73) Assignee: BASF SE, Ludwigshafen (DE)

( * ) Notice: Subject to any disclaimer, the term of this patent is extended or adjusted under 35 U.S.C. 154(b) by 97 days.

(21) Appl. No.: 14/895,704

(22) PCT Filed: May 28, 2014

(86) PCT No.: PCT/EP2014/061081
§ 371 (c)(1),
(2) Date: Dec. 3, 2015

(87) PCT Pub. No.: WO2014/195208
PCT Pub. Date: Dec. 11, 2014

(65) Prior Publication Data
US 2016/0122468 A1    May 5, 2016

(30) Foreign Application Priority Data

Jun. 3, 2013 (EP) ..................................... 13170256

(51) Int. Cl.
| | | |
|---|---|---|
| *A61K 47/34* | (2017.01) | |
| *A61K 8/85* | (2006.01) | |
| *A61Q 19/00* | (2006.01) | |
| *C08G 63/08* | (2006.01) | |
| *A61Q 19/10* | (2006.01) | |
| *C07C 69/68* | (2006.01) | |
| *A61K 8/37* | (2006.01) | |

(52) U.S. Cl.
CPC ............... *C08G 63/08* (2013.01); *A61K 8/37* (2013.01); *A61K 8/85* (2013.01); *A61K 47/34* (2013.01); *A61Q 19/00* (2013.01); *A61Q 19/10* (2013.01); *C07C 69/68* (2013.01); *A61K 2800/48* (2013.01)

(58) Field of Classification Search
CPC . A61K 8/37; A61K 8/85; A61K 47/34; A61Q 19/00; A61Q 19/10; C07C 69/68
See application file for complete search history.

(56) References Cited

U.S. PATENT DOCUMENTS

| | | |
|---|---|---|
| 3,098,795 A | 7/1963 | Kreps |
| 3,929,870 A | 12/1975 | David et al. |
| 5,399,353 A | 3/1995 | Bartnik et al. |
| 2005/0215453 A1 | 9/2005 | Teissier |
| 2009/0200511 A1* | 8/2009 | Allen .................. A61K 8/37 252/182.12 |

FOREIGN PATENT DOCUMENTS

| | | |
|---|---|---|
| CN | 101456812 A | 6/2009 |
| DE | 4003096 | 8/1991 |
| EP | 1378502 | 1/2004 |
| EP | 2792372 A1 | 10/2014 |
| GB | 804117 | 11/1955 |
| JP | 2005522570 A | 7/2005 |
| JP | 2009144127 A | 7/2009 |
| JP | 2010-59354 | 3/2010 |
| JP | 2010-169620 | 8/2010 |
| WO | WO-91/11504 | 8/1991 |
| WO | WO-03/016259 | 2/2003 |
| WO | WO-2008006058 A2 | 1/2008 |
| WO | WO-2008006076 A2 | 1/2008 |
| WO | WO-2013064059 A1 | 5/2013 |
| WO | WO-2014195210 | 12/2014 |

OTHER PUBLICATIONS

Koo et al. (Polym. Chem. Published Jan. 4, 2012, pp. 718-726).*
Alger (Polymer Science Dictionary, Second Edition, p. 124, 1989).*
PCT International Report on Patentability in PCT/EP2014/061081, dated Dec. 3, 2015, 3 pages.
English Translation of International Search Report in PCT/EP2014/061081 dated Sep. 23, 2014, 3 pgs.
Anonymous Authors, "Alkyl Lactyllactates and Processes of Making the Same and Applications Thereof," IP.com Journal, IP.COM Inc., West Henrietta, NY, US (Mar. 22, 2007).
Ohara, H., et al., "Lipase-Catalyzed Oligomerization and Hydrolysis of Alkyl lactates: Direct Evidence in the Catalysis Mechanism that Enantioselection is Governed by a Deacylation Step.," *Biomacromolecules* 11, No. 8 (2010), pp. 2008-2015.

* cited by examiner

*Primary Examiner* — Alma Pipic
(74) *Attorney, Agent, or Firm* — Marshall, Gerstein & Borun LLP

(57) ABSTRACT

Esters of oligo-hydroxycarboxylic acids have the general formula ( ):

(I)

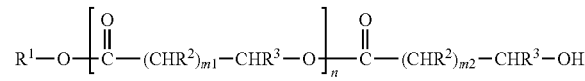

wherein at least one of the radicals $R^1$, $R^4$ or $R^5$ is a linear or branched aliphatic hydrocarbon radical having 6 to 30 carbon atoms and 0, 1, 2 or 3 double bonds. Cosmetic and pharmaceutical agents contain said esters. These esters are effective as thickeners, in particular for compositions containing surfactants.

13 Claims, No Drawings

ESTERS OF OLIGO-HYDROXYCARBOXYLIC ACIDS AND USE THEREOF

CROSS-REFERENCE TO RELATED APPLICATIONS

This application is the National Stage entry of PCT/EP2014/061081, filed on May 28, 2014, which claims priority to European Application Number 13170256.5, filed on Jun. 3, 2013, which is incorporated herein by reference in their entireties.

BACKGROUND OF THE INVENTION

The present invention relates to esters of oligohydroxycarboxylic acids, to cosmetic and pharmaceutical compositions which comprise these esters, and to the use of these esters as thickeners, specifically for surfactant-containing compositions.

PRIOR ART

Thickeners serve to increase the viscosity of flowable compositions. Thickeners are used widely for modifying the rheological properties of aqueous preparations, for example in the fields of cosmetics, pharmacy, detergents and cleaners, human and animal nutrition, etc. Customary thickeners as are used primarily in cosmetics are, for example, fatty alcohol alkoxylates, such as the ethoxylates of lauryl alcohol (INCI name Laureth x, where x is the degree of alkoxylation) or the esters of polyol alkoxylates with fatty acids, such as e.g. the trioleates of ethoxylated and/or propoxylated trimethylolpropane.

For many current applications, apart from having a good thickening effect, further requirements are placed on thickeners. Especially in cosmetics, it is often desired for the active ingredients and auxiliaries used to simultaneously satisfy two or more tasks, for example in addition to the thickening property, also have foam-stabilizing properties or serve as solubilizers for other components, such as UV filters. Furthermore, there is a need for thickeners which can be prepared at least in part from biogenic sources and specifically also renewable raw materials. Furthermore, there is also a need for thickeners which have no alkoxylated groups and which thus in particular render superfluous the use of ethylene oxide for their preparation.

DE 40 03 096 A1 describes sulfated hydroxycarboxylic acid esters and their use as surface-active substances. Example A described on page 4 of this document for the preparation of lauryl lactate is not practicable technical teaching for the preparation of lauryl esters of lactic acid oligomers. For example, it is not even possible to heat to the stated 225° C. the esterification using toluene as entrainer, which forms an azeotrope with a boiling point of about 80 to 90° C. with the water that is released during the reaction, using a water separator. This document also does not teach that non-sulfated hydroxycarboxylic acid esters, let alone esters of hydroxycarboxylic acid oligomers, are suitable as thickeners.

U.S. Pat. No. 3,098,795 describes cosmetic compositions for topical applications which comprise lactic acid esters of fatty alcohols. This document mentions neither specifically esters of lactic acid oligomers, nor a use as thickeners.

JP 2009-14127 describes the preparation of polylactides which react to give the corresponding polylactides in the first step as a result of ring-opening reaction of a L- or D-lactide in the presence of amidine bases and hydroxy compounds and in the second step as a result of bringing them into contact with a further L- or D-lactide. This document describes exclusively reactions of lactides, i.e. of cyclic diesters of lactic acid. The resulting products differ in structural terms from products which are prepared starting from monolactic acid. Polylactides prepared from lactides firstly automatically always have a degree of oligomerization greater than two and, secondly, all of the individual molecules present have two repeat units or a whole-numbered multiple of two. Furthermore, the described polylactides have a very high number of repeat units and accordingly a high molecular weight.

JP 2010-059354 describes polylactic acid compounds which consist of polylactic acid block copolymers. These are obtained by polymerization reactions of L- or D-lactide. The products obtained in this way differ in structural terms from those which are prepared starting from monolactic acid.

EP 1378502 describes the preparation and isolation of oligolactate esters with a certain chain length as an individual compound which have an esterified terminal carboxy group and a degree of condensation of 3 to 20. The described oligolactate esters are obtained by reacting a L- or D-lactide with an ester compound in the presence of an alkyl alkali metal.

GB 804,117 describes lactic acid derivatives which are obtained by heating a lactide with monovalent or polyvalent aliphatic, cycloaliphatic or arylaliphatic alcohols in the presence of an acid catalyst.

WO 03/016259 describes compounds which are composed of repeating lactic acid units which have uniform or different configurations on the chirality center. The described compounds are prepared from lactic acid oligomers or lactic acid dimers.

WO 91/11504 describes anionic surfactants which are obtainable from hydroxycarboxylic acids by reaction with sulfating agents with subsequent neutralization with aqueous bases.

Thomson Scientific, London, GB database Week 201335 describes a medical adhesive consisting of mono- and cyanoacrylates.

The object of the present invention is to provide novel compounds which are advantageously suitable as thickeners for a variety of applications. Specifically, they should be suitable for covering a complex spectrum of requirements, as described at the start. In particular, it should be possible to provide thickeners for surfactant-containing formulations which have good rheology-modifying properties, which are at least comparable with thickeners based on petrochemical components and/or based on alkylene oxides and known from the prior art.

Surprisingly, it has now been found that this object is achieved by esters of oligo-hydroxycarboxylic acids.

SUMMARY OF THE INVENTION

The invention firstly provides compounds of the general formula (I)

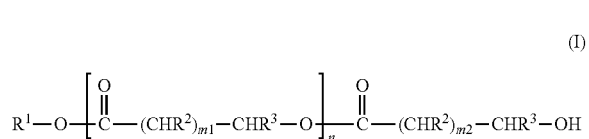

(I)

in which $R^1$ is hydrogen or a linear or branched aliphatic hydrocarbon radical having 1 to 30 carbon atoms and 0, 1, 2 or 3 double bonds, the radicals $R^2$, independently of one another, are selected from hydrogen, methyl, ethyl, —OH, —COOR$^4$, —CH$_2$—OH and —CH$_2$—COOR$^4$, where the radicals $R^4$ are hydrogen or a linear or branched aliphatic hydrocarbon radical having 1 to 30 carbon atoms and 0, 1, 2 or 3 double bonds, the radicals $R^3$, independently of one another, are selected from hydrogen, methyl, ethyl, —OH, —COOR$^5$, —CH$_2$—OH and —CH$_2$—COOR$^5$, where the radicals $R^5$ are hydrogen or a linear or branched aliphatic hydrocarbon radical having 1 to 30 carbon atoms and 0, 1, 2 or 3 double bonds, n is on average a value of at least 0.1, m1 and m2, independently of one another, are 0 or 1, with the proviso that at least one of the radicals $R^1$, $R^4$ or $R^5$ is a linear or branched aliphatic hydrocarbon radical having 1 to 30 carbon atoms and 0, 1, 2 or 3 double bonds.

A preferred embodiment covers esters of oligolactate. According to this, the compounds of the general formula (I) are selected from compounds of the formula (I.1)

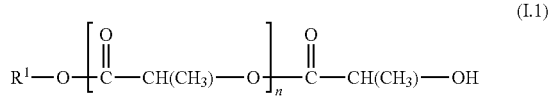

(I.1)

in which $R^1$ is hydrogen or a linear or branched hydrocarbon radical having 1 to 30 carbon atoms and 0, 1, 2 or 3 double bonds, and n is on average a value of at least 0.1.

The invention further provides a process for preparing compounds of the general formula (I). The invention also provides the compounds of the general formula (I) obtainable by this process.

The invention further provides a cosmetic or pharmaceutical composition which comprises at least one compound of the general formula (I), as defined above and below.

The invention further provides the use of compounds of the general formula (I), as defined above and below, as thickeners for aqueous surfactant-containing compositions.

The invention further provides the use of compounds of the general formula (I), as defined above and below, as a component for the formulation of cosmetic compositions,
pharmaceutical compositions,
detergents and cleaners,
crop protection compositions,
wetting agents,
paints, coatings, adhesives, leather-treatment or textile-treatment compositions, etc.

DESCRIPTION OF THE INVENTION

The compounds of the general formula (I) can be present in the form of mixtures or as pure compounds. As a rule, mixtures of compounds of the general formula (I), as are obtainable e.g. by the preparation process described below, are suitable for the uses according to the invention. The individual components of these mixtures can differ for example as regards the degree of oligomerization n. If hydroxycarboxylic acids which have more than one carboxyl group and/or more than one alcoholic OH group are used for preparing the compounds of the general formula (I), then the individual components of these mixtures may also be structural isomers from the esterification reaction for their preparation. It is of course also possible to separate the reaction mixtures obtainable by the process according to the invention using customary separation processes, e.g. by distillation or chromatography.

The average degree of oligomerization arises for the inventive compounds of the general formula (I) and of the general formula (I.1) by adding 1 to the value of the variables n.

Suitable linear or branched aliphatic hydrocarbon radicals having 1 to 30 carbon atoms and 0, 1, 2 or 3 double bonds are the corresponding $C_1$-$C_{30}$-alkyl radicals, $C_1$-$C_{30}$-alkenyl radicals, $C_1$-$C_{30}$-alkadienyl radicals and $C_1$-$C_{30}$-alkatrienyl radicals.

Preferably, at least one of the radicals $R^1$, $R^4$ or $R^5$ is a linear or branched aliphatic hydrocarbon radical having 1 to 30 carbon atoms and 0, 1, 2 or 3 double bonds. In particular, $R^1$, $R^4$ and $R^5$, independently of one another, are selected from methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethyl-propyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, etc.

In a preferred embodiment, at least one of the radicals $R^1$, $R^4$ or $R^5$ is a linear or branched aliphatic hydrocarbon radical having 6 to 30 carbon atoms and 0, 1, 2 or 3 double bonds. Particularly preferably, $R^1$, $R^4$ and $R^5$, independently of one another, are selected from n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, and combinations thereof.

The radicals $R^1$, $R^4$ and $R^5$ can be derived from pure alcohols or from alcohol mixtures. Preference is given to alcohols or alcohol mixtures that are available on an industrial scale. In a preferred embodiment, $R^1$, $R^4$ and $R^5$ are then, independently of one another, selected from predominantly linear alkyl, alkenyl, alkadienyl and alkatrienyl radicals, as occur in natural or synthetic fatty acids and the corresponding fatty alcohols.

In a further preferred embodiment, $R^1$, $R^4$ and $R^5$, independently of one another, are derived from fatty alcohols which are based on industrial alcohol mixtures. These include e.g. the alcohol mixtures that are produced during the hydrogenation of industrial methyl esters based on fats and oils. Furthermore, these include the alcohol mixtures (oxoalcohols) that are produced during the hydrogenation of aldehydes from the oxo synthesis or the alcohol mixtures that are produced during the dimerization of unsaturated fatty alcohols.

Preferably, at least one of the radicals $R^1$, $R^4$ and $R^5$ is derived from linear saturated alcohols having 8 to 18 carbon atoms.

Particularly preferably, at least one of the radicals $R^1$, $R^4$ and $R^5$ is derived from a mixture of linear saturated $C_{12}$-/$C_{14}$-alcohols.

Furthermore, at least one of the radicals $R^1$, $R^4$ and $R^5$ is preferably derived from a $C_{16}$-/$C_{18}$-fatty alcohol mixture. Mixtures of cetyl (hexadecyl) and stearyl (octadecyl) are also referred to as cetearyl.

Preferably, the variables m1 and m2 have the same meaning in the compounds (I).

The compounds of the general formula (I) are esters of oligohydroxycarboxylic acids. These can also be derived from customary hydroxycarboxylic acids, such as lactic acid, glycolic acid, malic acid, tartaric acid, tartronic acid and mixtures thereof. Preferably, the compounds (I) are derived from lactic acid, glycolic acid, malic acid, tartaric acid or mixtures thereof. The compounds (I) are particularly preferably derived from lactic acid.

In the compounds of the general formula (I), n is preferably a value from 0.1 to 100, particularly preferably from 0.15 to 50, in particular from 0.2 to 20.

In the compounds of the general formula (I.1), n is preferably a value from 0.1 to 100, particularly preferably from 0.15 to 50, in particular from 0.2 to 20, very particularly preferably 0.2 to 10.

The compounds of the general formula (I) are in particular not lactides, i.e. cyclic dimers of lactic acid, and polylactides.

The invention further provides a process for preparing compounds of the general formula (I), in which at least one hydroxycarboxylic acid of the general formula (I.A)

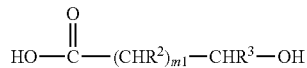
(I.A)

in which
the radicals $R^2$, independently of one another, are selected from hydrogen, methyl, ethyl, —OH, —COOR$^4$, —CH$_2$—OH and —CH$_2$—COOR$^4$, where the radicals $R^4$ are hydrogen or a linear or branched aliphatic hydrocarbon radical having 1 to 30 carbon atoms and 0, 1, 2 or 3 double bonds,
the radicals $R^3$, independently of one another, are selected from hydrogen, methyl, ethyl, —OH, —COOR$^5$, —CH$_2$—OH and —CH$_2$—COOR$^5$, where the radicals $R^5$ are hydrogen or a linear or branched aliphatic hydrocarbon radical having 1 to 30 carbon atoms and 0, 1, 2 or 3 double bonds,
m1 is 0 or 1,
$R^1$ is reacted in an esterification reaction, where the esterification takes place in the presence of at least one alcohol $R^1$—OH, where
$R^1$ is hydrogen or a linear or branched aliphatic hydrocarbon radical having 1 to 30 carbon atoms and 0, 1, 2 or 3 double bonds,
or the product of the esterification of the hydroxycarboxylic acid(s) (I.A) is then reacted with at least one alcohol $R^1$—OH.

As regards suitable and preferred definitions of $R^1$, $R^2$, $R^3$, $R^4$, $R^5$ and m1, reference is made to the previous statements relating to these radicals and variables in their entirety.

The invention further provides a composition which comprises a mixture of compounds of the general formula (I)

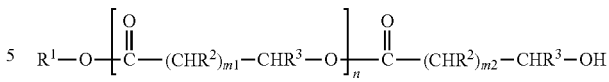
(I)

in which
$R^1$ is hydrogen or a linear or branched aliphatic hydrocarbon radical having 1 to 30 carbon atoms and 0, 1, 2 or 3 double bonds,
$R^2$ independently of one another, are selected from hydrogen, methyl, ethyl, —OH, —COOR$^4$, —CH$_2$—OH and —CH$_2$—COOR$^4$, where the radicals $R^4$ are hydrogen or a linear or branched aliphatic hydrocarbon radical having 1 to 30 carbon atoms and 0, 1, 2 or 3 double bonds,
$R^3$ independently of one another, are selected from hydrogen, methyl, ethyl, —OH, —COOR$^5$, —CH$_2$—OH and —CH$_2$—COOR$^5$, where the radicals $R^5$ are hydrogen or a linear or branched aliphatic hydrocarbon radical having 1 to 30 carbon atoms and 0, 1, 2 or 3 double bonds,
n is on average a value from 0.1 to 100,
m1 and m2, independently of one another, are 0 or 1,
with the proviso that at least one of the radicals $R^1$, $R^4$ or $R^5$ is a linear or branched aliphatic hydrocarbon radical having 1 to 30 carbon atoms and 0, 1, 2 or 3 double bonds,
obtainable by a process in which at least one hydroxycarboxylic acid of the general formula (I.A)

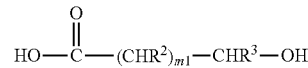
(I.A)

in which
$R^2$ independently of one another, are selected from hydrogen, methyl, ethyl, —OH, —COOR$^4$, —CH$_2$—OH and —CH$_2$—COOR$^4$, where the radicals $R^4$ are hydrogen or a linear or branched aliphatic hydrocarbon radical having 1 to 30 carbon atoms and 0, 1, 2 or 3 double bonds,
$R^3$ independently of one another, are selected from hydrogen, methyl, ethyl, —OH, —COOR$^5$, —CH$_2$—OH and —CH$_2$—COOR$^5$, where the radicals $R^5$ are hydrogen or a linear or branched aliphatic hydrocarbon radical having 1 to 30 carbon atoms and 0, 1, 2 or 3 double bonds,
m1 is 0 or 1,
$R^1$ is reacted in an esterification reaction, where the esterification takes place in the presence of at least one alcohol $R^1$—OH, where
$R^1$ is hydrogen or a linear or branched aliphatic hydrocarbon radical having 1 to 30 carbon atoms and 0, 1, 2 or 3 double bonds,
or the product of the esterification of the hydroxycarboxylic acid(s) (I.A) is then reacted with at least one alcohol $R^1$—OH.

The esterification reaction can take place in several stages, in which case firstly at least one hydroxycarboxylic acid (I.A) is subjected to an esterification with oligomerization and then the resulting reaction mixture, optionally after a separation and/or purification, is reacted in a further esterification with at least one alcohol $R^1$—OH.

Preferably, the esterification reaction for preparing compounds of the general formula (I) takes place in the sense of a one-pot reaction in which at least one hydroxycarboxylic acid of the general formula (I.A) is subjected to an esterification in the presence of at least one alcohol $R^1$—OH.

The esterification reaction can take place in accordance with generally known processes, it being possible for the water of reaction that is formed to be removed e.g. by means of water-withdrawing agents, by extraction or by distillation.

Preferably, the water of reaction that is formed is removed by distillation. In a specific embodiment, the water of reaction that is formed is removed azeotropically. The reaction takes place in this connection in the presence of a solvent which forms an azeotropic mixture with water. Suitable solvents and entrainers are aliphatic and aromatic hydrocarbons, e.g. alkanes, such as n-hexane and n-heptane, cycloalkanes, such as cyclohexane and methylcyclohexane, aromatics, such as benzene, toluene and xylene isomers and so-called special-boiling-point spirits which have boiling points between 70 and 140° C. Particularly preferred entrainers are cyclohexane, methylcyclohexane and toluene. Suitable apparatuses for the azeotropic distillation with the elimination of the water of reaction and recycle of the solvent to the reaction vessel are known to the person skilled in the art. The solvent used can be removed from the reaction mixture after the esterification by means of customary methods, such as e.g. by distillation, optionally under reduced pressure.

If an alcohol $R^1$—OH with a sufficiently high boiling point is used for the esterification, e.g. a saturated or mono- or polyunsaturated fatty alcohol with at least 6 carbon atoms, then it is possible to dispense with the use of an entrainer during the distillative removal of the water of reaction.

The esterification temperature is generally in a range from about 50 to 250° C., particularly preferably from 70 to 200° C.

The esterification preferably takes place under atmospheric pressure or reduced pressure. For the distillative removal of the water of reaction, it is advantageous to carry out the esterification under reduced pressure. Preferably, the pressure during the esterification is in a range from 1 mbar to 1.1 bar, in particular 5 mbar to 1 bar, specifically 10 mbar to 900 mbar. This is true both for the single-stage variant of the esterification reaction described above and also for the two-stage variant.

The esterification can take place autocatalytically or in the presence of a catalyst. Suitable catalysts are strong acids, such as e.g. sulfuric acid, anhydrous hydrogen chloride, sulfonic acids, e.g. toluenesulfonic acid and methanesulfonic acid, and acidic ion exchangers. In the process according to the invention, sulfuric acid and p-toluenesulfonic acid is preferably used as catalyst. The amount of esterification catalyst here is generally in a range from about 0.1 to 5% by weight, based on the total amount of components to be esterified.

Preferably, the esterification reaction takes place without the addition of an external solvent. This is true both for the single-stage variant of the esterification reaction described above and also the second-stage variant. However, it is alternatively possible to carry out the reaction according to the invention in the presence of an organic solvent that is inert under the reaction conditions, or a solvent mixture. Preference is given to aprotic solvents. The solvents used preferably have a boiling point of at least 120° C., in particular of at least 140° C. These include e.g. alkylene glycol dialkyl ethers such as ethylene glycol dimethyl ether, ethylene glycol diethyl ether, etc. Cyclohexanone (b.p.: 155° C.), N-methylpyrrolidone (b.p.: 204° C.), sulfolane (b.p.: 285° C.), nitrobenzene (b.p.: 210° C.), xylene (b.p.: 140° C.), for example, are likewise suitable.

The desired average degree of oligomerization (p=1+n) is established in the customary manner.

Thus, in the case of the two-stage variant of the esterification reaction described above, firstly an oligomeric hydroxycarboxylic acid with the desired average degree of oligomerization (p=1+n) can be prepared. For this purpose, the reaction mixture is left under water-withdrawing conditions for a period at the reaction temperature which suffices to achieve the desired average degree of oligomerization. Preferably, the reaction time is about 0.5 to about 24 hours, in particular about 1 to about 20 hours. The oligomeric hydroxycarboxylic acid obtained in this way is then reacted with at least one alcohol $R^1$—OH to give the end product. The molar ratio of alcohol component $R^1$—OH to oligomeric hydroxycarboxylic acid for this variant is about 1:1.

In the case of the single-stage variant of the esterification reaction described above, at least one hydroxycarboxylic acid of the general formula (I.A) is subjected to an esterification in the presence of at least one alcohol $R^1$—OH. According to this variant, the desired average degree of oligomerization n is established for example via the molar ratio of alcohol component $R^1$—OH to hydroxycarboxylic acid (I.A). For this variant, this is preferably 1:1.01 to 1:200, particularly preferably 1:1.1 to 1:100, in particular 1:1.15 to 1:50, specifically 1:1.2 to 1:20. Also in accordance with this variant, the reaction mixture is left under water-withdrawing conditions for a period at a reaction temperature which suffices to achieve compounds of the general formula (I) with the desired average degree of oligomerization. Preferably, the reaction time is about 0.5 to about 24 hours, in particular about 1 to about 20 hours.

The compounds of the general formula (I) and of the general formula (I.1) are advantageously suitable for modifying the rheological properties of aqueous compositions. These may be quite generally for example cosmetic compositions, pharmaceutical compositions, hygiene products, coatings, compositions for the paper industry and the textile industry.

The compounds of the general formula (I) and of the general formula (I.1) are preferably suitable for thickening the consistency of surfactant-containing aqueous compositions in a wide range. They function here specifically as so-called "micellar thickeners", i.e. interface-active compounds which are used for increasing the viscosity of surfactant-containing formulations. Depending on the basic consistency of the liquid compositions, flow properties from thin-liquid ranging to solid (in the sense of "no longer flowing") can generally be achieved depending on the amount of copolymer used.

Surfactant-Containing Composition

The compounds of the general formula (I) or of the general formula (I.1) according to the invention are particularly advantageously suitable for formulating surfactant-containing compositions. In particular, these are aqueous surfactant-containing compositions. The compounds (I) and (I.1) are characterized in such compositions by their good thickening effect, even when used in small amounts.

The surfactant-containing compositions according to the invention preferably have a total surfactant content of from 0.1 to 75% by weight, particularly preferably from 0.5 to 60% by weight, in particular from 1 to 50% by weight, based on the total weight of the surfactant-containing composition. Specifically, the total surfactant content is in a range from 5 to 20% by weight.

Suitable surfactants are anionic surfactants, nonionic surfactants, cationic surfactants, amphoteric surfactants and mixtures thereof.

Typical examples of anionic surfactants are soaps, alkylsulfonates, alkylbenzenesulfonates, olefinsulfonates, alkyl ether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as for example acyl glutamates and acyl aspartates, and also acyl lactylates, acyl tartrates, alkyl oligoglucosidesulfates, alkyl-glucosecarboxylates, protein fatty acid condensates and alkyl (ether) phosphates.

Suitable soaps are e.g. alkali metal, alkaline earth metal and ammonium salts of fatty acids, such as potassium stearate.

Suitable olefinsulfonates are obtained e.g. by the addition reaction of $SO_3$ onto olefins of the formula $R^3$—CH=CH—$R^4$ and subsequent hydrolysis and neutralization, where $R^3$ and $R^4$, independently of one another, are H or alkyl radicals having 1 to 20 carbon atoms, with the proviso that $R^3$ and $R^4$ together have at least 6 and preferably 8 to 20, specifically 10 to 16, carbon atoms. As regards preparation and use, reference may be made to the review article "J. Am. Oil. Chem. Soc.", 55, 70 (1978). The olefinsulfonates can be in the form of alkali metal, alkaline earth metal, ammonium, alkylammonium, alkanolammonium or glucammonium salts. Preferably, the olefinsulfonates are in the form of sodium salts. The hydrolyzed alpha-olefinsulfonation product, i.e. the alpha-olefinsulfonates, are composed of ca. 60% by weight of alkanesulfonates and ca. 40% by weight of hydroxyalkanesulfonates; of this, about 80 to 85% by weight are monosulfonates and 15 to 20% by weight are disulfonates.

Preferred methyl ester sulfonates (MES) are obtained by sulfonation of the fatty acid methyl esters of vegetable or animal fats or oils. Preference is given to methyl ester sulfonates from vegetable fats and oils, e.g. from rapeseed oil, sunflower oil, soybean oil, palm oil, coconut fat, etc.

Preferred alkyl sulfates are sulfates of fatty alcohols of the general formula $R^6$—O—$SO_3Y$, in which $R^6$ is a linear or branched, saturated or unsaturated hydrocarbon radical having 6 to 22 carbon atoms and Y is an alkali metal, the monovalent charge equivalent of an alkaline earth metal, ammonium, mono-, di-, tri- or tetralkylammonium, alkanolammonium or glucammonium. Suitable fatty alcohol sulfates are preferably obtained by sulfation of native fatty alcohols or synthetic oxoalcohols and subsequent neutralization. Typical examples of fatty alcohol sulfates are the sulfation products of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, behenyl alcohol and elaeostearyl alcohol, and the salts and mixtures thereof. Preferred salts of the fatty alcohol sulfates are the sodium and potassium salts, in particular the sodium salts. Preferred mixtures of the fatty alcohol sulfates are based on industrial alcohol mixtures which are formed e.g. during the high-pressure hydrogenation of industrial methyl esters based on fats and oils or during the hydrogenation of aldehydes from the oxo synthesis or during the dimerization of unsaturated fatty alcohols. Preference is given to using fatty alcohols and fatty alcohol mixtures having 12 to 18 carbon atoms and in particular 16 to 18 carbon atoms for the preparation of alkyl sulfates. Typical examples thereof are industrial alcohol sulfates based on vegetable raw materials.

Preferred sarcosinates are sodium lauroyl sarcosinate or sodium stearoyl sarcosinate.

Preferred protein fatty acid condensates are wheat-based vegetable products.

Preferred alkylphosphates are alkyl esters of mono- and diphosphoric acid.

Suitable acylglutamates are compounds of the formula (I)

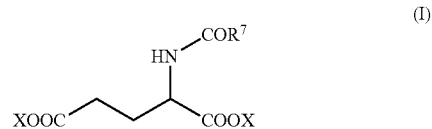

in which $COR^7$ is a linear or branched acyl radical having 6 to 22 carbon atoms and 0, 1, 2 or 3 double bonds and X is hydrogen, an alkali metal, the monovalent charge equivalent of an alkaline earth metal, ammonium, alkylammonium, alkanolammonium or glucammonium. The preparation of acylglutamates takes place for example by means of the Schotten-Baumann acylation of glutamic acid with fatty acids, fatty acid esters or fatty acid halides. Acylglutamates are commercially available for example from BASF SE, Clariant AG, Frankfurt/DE, or from Ajinomoto Co. Inc., Tokyo/JP. An overview of the preparation and properties of the acylglutamates can be found by M. Takehara et al. in J. Am. Oil Chem. Soc. 49 (1972) 143. Typical acylglutamates suitable as component b) are preferably derived from fatty acids having 6 to 22 and particularly preferably 12 to 18 carbon atoms. The mono- or dialkali metal salts of the acylglutamate, in particular, are used. These include e.g. (trade name of Ajinomoto, USA in brackets): sodium cocoyl glutamate (Amisoft CS-11), disodium cocoyl glutamate (Amisoft ECS-22SB), triethanolammonium cocoyl glutamate (Amisoft CT-12), triethanolammonium lauroyl glutamate (Amisoft LT-12), sodium myristoyl glutamate (Amisoft MS-11), sodium stearoyl glutamate (Amisoft HS-11 P) and mixtures thereof.

The nonionic surfactants include, for example:
fatty alcohol polyoxyalkylene esters, for example lauryl alcohol polyoxyethylene acetate,
alkyl polyoxyalkylene ethers which are derived from low molecular weight $C_1$-$C_6$-alcohols or from $C_7$-$C_{30}$-fatty alcohols. Here, the ether component can be derived from ethylene oxide units, propylene oxide units, 1,2-butylene oxide units, 1,4-butylene oxide units and random copolymers and block copolymers thereof. These include specifically fatty alcohol alkoxylates and oxoalcohol alkoxylates, in particular of the type RO—$(R^8O)_r(R^9O)_sR^{10}$ where $R^8$ and $R^9$ independently of one another =$C_2H_4$, $C_3H_6$, $C_4H_8$ and $R^{10}$=H, or $C_1$-$C_{12}$-alkyl, R=$C_3$-$C_{30}$-alkyl or $C_6$-$C_{30}$-alkenyl, r and s independently of one another are 0 to 50, where both cannot be 0, such as isotridecyl alcohol and oleyl alcohol polyoxyethylene ethers,
alkylarylalcohol polyoxyethylene ethers, e.g. octylphenol polyoxyethylene ether,
alkoxylated animal and/or vegetable fats and/or oils, for example corn oil ethoxylates, castor oil ethoxylates, tallow fatty ethoxylates,
glycerol esters, such as, for example glycerol monostearate, alkylphenol alkoxylates, such as, for example, ethoxylated isooctyl-, octyl- or nonylphenol, tributylphenol polyoxyethylene ether, fatty amine alkoxylates, fatty acid amide and fatty acid diethoanolamide alkoxylates, in particular ethoxylates thereof, sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides, alkyl methylsulfoxides, alkyldimethylphosphine oxides, such as, for example, tetradecyldimethylphosphine oxide.

Suitable amphoteric surfactants are e.g. alkylbetaines, alkylamidopropylbetaines, alkyl-sulfobetaines, alkyl glycinates, alkyl carboxyglycinates, alkyl amphoacetates or -propionates, alkyl amphodiacetates or -dipropionates. For example, cocodimethylsulfopropylbetaine, laurylbetaine, cocamidopropylbetaine, sodium cocamphopropionate or tetradecyldimethylamine oxide can be used.

The cationic surfactants include, for example, quaternized ammonium compounds, in particular alkyltrimethylammonium and dialkyldimethylammonium halides and alkylsulfates, and pyridine and imidazoline derivatives, in particular alkylpyridinium halides. For example, behenyl or cetyltrimethylammonium chloride can be used. Also of suitability are so-called ester quats which are based on quaternary triethanol-methyl-ammonium or quaternary diethanol-dimethyl-ammonium compounds with long hydrocarbon chains in the form of fatty acid esters. These include, for example, bis(acyloxyethyl)hydroxyethylammonium methosulfate. Also of suitability is Dehyquart L 80 (INCI: Dicocoylethyl Hydroxyethylmonium Methosulfate (and) Propylene Glycol).

Cosmetic and Pharmaceutical Compositions

The compounds of the general formula (I) and of the general formula (I.1) are preferably suitable for formulating cosmetic and pharmaceutical products, specifically aqueous cosmetic and pharmaceutical products.

The invention further provides a cosmetic or pharmaceutical composition comprising a) at least one compound of the general formula (I), as defined above, b) at least one cosmetically or pharmaceutically acceptable active ingredient, and c) optionally at least one cosmetically or pharmaceutically acceptable auxiliary that is different from components a) and b).

Preferably, at least one compound of the general formula (I.1) is used as component a).

Preferably, the component c) comprises at least one cosmetically or pharmaceutically acceptable carrier.

Preferably, the carrier component c) is selected from i) water, ii) water-miscible organic solvents, preferably $C_2$-$C_4$-alkanols, in particular ethanol, iii) oils, fats, waxes, iv) esters of $C_6$-$C_{30}$-monocarboxylic acids with mono-, di- or trihydric alcohols that are different from iii), v) saturated acyclic and cyclic hydrocarbons, vi) fatty acids, vii) fatty alcohols, viii) propellant gases, and mixtures thereof.

Suitable hydrophilic components c) are the aforementioned organic solvents, oils and fats.

Specifically suitable cosmetically compatible oil or fat components c) are described in Karl-Heinz Schrader, Grundlagen and Rezepturen der Kosmetika [Fundamentals and formulations of cosmetics], 2nd edition, Verlag Hüthig, Heidelberg, pp. 319-355, to which reference is hereby made.

The cosmetic compositions according to the invention may be skin cosmetic, hair cosmetic, dermatological, hygiene or pharmaceutical compositions. On account of their thickening properties, the compounds of the formula (I) and of the formula (I.1) described above are suitable particularly as additives for hair and skin cosmetics.

Preferably, the compositions according to the invention are in the form of a foam, spray, ointment, cream, emulsion, suspension, lotion, milk or paste. If desired, liposomes or microspheres can also be used.

The cosmetic compositions according to the invention can additionally comprise cosmetically and/or dermatologically active ingredients and effect substances and also auxiliaries. Preferably, the cosmetic compositions according to the invention comprise at least one compound of the formula (I) or of the formula (I.1), as defined above, at least one carrier C) as defined above and at least one constituent different therefrom which is preferably selected from cosmetically active ingredients, emulsifiers, surfactants, preservatives, perfume oils, additional thickeners, hair polymers, hair and skin conditioners, graft polymers, water-soluble or dispersible silicone-containing polymers, photoprotective agents, bleaches, gel formers, care agents, tinting agents, tanning agents, dyes, pigments, consistency regulators, humectants, refatting agents, collagen, protein hydrolyzates, lipids, antioxidants, defoamers, antistats, emollients and softeners.

In addition to the compounds of the formula (I) and of the formula (I.1), the cosmetic compositions can comprise at least one conventional thickener. These include e.g. polysaccharides and organic sheet minerals such as Xanthan Gum® (Kelzan® from Kelco), Rhodopol® 23 (Rhone Poulenc) or Veegum® (R. T. Vanderbilt) or Attaclay® (Engelhardt). Suitable thickeners are also organic natural thickeners (agar agar, carrageenan, tragacanth, gum arabic, alginates, pectins, polyoses, guar flour, carob seed flour, starch, dextrins, gelatin, casein) and inorganic thickeners (polysilicic acids, clay minerals such as montmorillonites, zeolites, silicas). Further thickeners are polysaccharide gums, for example gum arabic, agar, alginates, carrageenans and their salts, guar, guaran, tragacanth, gellan, ramsan, dextran or xanthan and their derivatives, e.g. propoxylated guar, and their mixtures. Other polysaccharide thickeners are for example starches of highly diverse origin and starch derivatives, e.g. hydroxyethyl starch, starch phosphate esters or starch acetates, or carboxymethylcellulose or its sodium salt, methyl-, ethyl-, hydroxyethyl-, hydroxypropyl-, hydroxy-propyl-methyl- or hydroxyethyl-methyl-cellulose or cellulose acetate. Thickeners which can be used are also sheet silicates. These include for example the magnesium or sodium-magnesium sheet silicates from Solvay Alkali available under the trade name Laponite®, as well as the magnesium silicates from Sud-Chemie.

Suitable cosmetically and/or dermatologically active ingredients are e.g. skin and hair pigmentation agents, tanning agents, bleaches, keratin-hardening substances, antimicrobial active ingredients, light filter active ingredients, repellant active ingredients, hyperemic substances, keratolytic and keratoplastic substances, antidandruff active ingredients, antiphlogistics, keratinizing substances, active ingredients that have an antioxidative effect and/or act as free-radical scavengers, skin-moisturizing or -humectant substances, refatting active ingredients, deodorizing active ingredients, sebostatic active ingredients, plant extracts, antierythematous or antiallergic active ingredients and mixtures thereof.

Artificially skin-tanning active ingredients which are suitable for tanning the skin without natural or artificial irradiation with UV rays are e.g. dihydroxyacetone, alloxan and walnut shell extract. Suitable keratin-hardening substances are generally active ingredients as are also used in antiperspirants, such as e.g. potassium aluminum sulfate, aluminum hydroxychloride, aluminum lactate, etc. Antimicrobial active ingredients are used in order to destroy microorganisms or to inhibit their growth and thus serve both as preservatives and as deodorizing substance which reduces the formation or the intensity of body odor. These include e.g. customary preservatives known to the person skilled in the art, such as p-hydroxybenzoic acid esters, imidazolidinylurea, formaldehyde, sorbic acid, benzoic acid, salicylic acid, etc. Deodorizing substances of this kind are e.g. zinc ricinoleate, triclosan, undecylenic acid alkylolamides, citric acid triethyl esters, chlorhexidine, etc. Suitable light filter active ingredients are substances which absorb UV rays in the UV-B and/or UV-A region. Also of suitability are p-aminobenzoic acid esters, cinnamic acid esters, benzophenones, camphor derivatives, and pigments that stop UV rays, such as titanium dioxide, talc and zinc oxide. Suitable repellant active ingredients are compounds which are able to keep away or repel certain animals, in particular insects, from people. These include e.g. 2-ethyl-1,3-hexanediol, N,N-diethyl-m-toluamide, etc. Suitable hyperemic substances, which stimulate blood flow through the skin, are e.g. essential oils, such as dwarf-pine, lavender, rosemary, juniper berry, horse chestnut extract, birch leaf extract, hay flower extract, ethyl acetate, camphor, menthol, peppermint oil, rosemary extract, eucalyptus oil, etc. Suitable keratolytic and keratoplastic substances are e.g. salicylic acid, calcium thioglycolate, thioglycolic acid and its salts, sulfur, etc. Suitable antidandruff active ingredients are e.g. sulfur, sulfur polyethylene glycol sorbitan monooleate, sulfur ricinol polyethoxylate, zinc pyrithione, aluminum pyrithione, etc. Suitable antiphologistics, which counteract skin irritations are, e.g. allontoin, bisabolol, dragosantol, chamomile extract, panthenol, etc.

The cosmetic compositions according to the invention can comprise at least one cosmetically or pharmaceutically acceptable polymer as cosmetic active ingredient (and also optionally as auxiliary). These include quite generally anionic, cationic, amphoteric and neutral polymers.

Examples of anionic polymers are copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional, t-butyl acrylate, methacrylic acid (e.g. Luviskol® VBM), copolymers of acrylic acid and methacrylic acid with hydrophobic monomers, such as e.g. $C_4$-$C_{30}$-alkyl esters of (meth)acrylic acid, $C_4$-$C_{30}$-alkyl vinyl esters, $C_4$-$C_{30}$-alkyl vinyl ethers and hyaluronic acid. One example of an anionic polymer is also the methyl methacrylate/methacrylic acid/acrylic acid/urethane acrylate copolymer available under the name Luviset® Shape (INCI name: Polyacrylate-22). Examples of anionic polymers are also vinyl acetate/crotonic acid copolymers, as are commercially available for example under the names Resyn® (National Starch) and Gafset® (GAF), and vinylpyrrolidone/vinyl acrylate copolymers, available for example under the trade name Luviflex® (BASF). Further suitable polymers are vinylpyrrolidone/acrylate terpolymer available under the name Luviflex® VBM-35 (BASF) and sodium-sulfonate-containing polyamides or sodium-sulfonate-containing polyesters. Also of suitability are vinylpyrrolidone/ethyl methacrylate/methacrylic acid copolymers as sold by Stepan under the names Stepanhold-Extra and —R1 and the Carboset® grades from BF Goodrich.

Suitable cationic polymers are e.g. cationic polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcapro-lactam/N-vinylpyrrolidone/N-vinylimidazolium salts (Luviquat® Hold); cationic cellulose derivatives (Polyquaternium-4 and -10), acrylamide copolymers (Polyquaternium-7) and chitosan. Suitable cationic (quaternized) polymers are also Merquat® (polymer based on dimethyldiallylammoniumchloride), Gafquat® (quaternary polymers which are formed by the reaction of polyvinylpyrrolidone with quaternary ammonium compounds), polymer JR (hydroxyethylcellulose with cationic groups) and plant-based cationic polymers, e.g. guar polymers, such as the Jaguar® grades from Rhodia.

Very particularly suitable polymers are neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include for example Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF SE), or polyvinylpyrrolidone and copolymers thereof, in particular with vinyl esters, such as vinyl acetate, e.g. Luviskol® VA 37, VA 55, VA 64, VA 73 (BASF SE); polyamides, e.g. based on itaconic acid and aliphatic diamines, as are described e.g. in DE-A-43 33 238.

Suitable polymers are also amphoteric or zwitterionic polymers, such as the octyl-acrylamide/methyl methacrylate/tert-butylaminoethyl methacrylate/2-hydroxypropyl methacrylate copolymers obtainable under the names Amphomer® (National Starch), and also zwitterionic polymers, as are disclosed for example in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethyl-betaine/methacrylate copolymers which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

In a specific embodiment, the compositions according to the invention comprise at least one polymer which acts as a thickener.

Suitable polymeric thickeners are, for example, optionally modified polymeric natural materials (carboxymethylcellulose and other cellulose ethers, hydroxyethyl- and -propylcellulose and the like), and synthetic polymeric thickeners (polyacrylic and polymethacrylic compounds, vinyl polymers, polycarboxylic acids, polyethers, polyimines, polyamides). These include the in part aforementioned polyacrylic and polymethacrylic compounds, for example the high molecular weight homopolymers of acrylic acid crosslinked with a polyalkenyl polyether, in particular an allyl ether of sucrose, pentaerythritol or propylene (INCI name: Carbomer). Such polyacrylic acids are available inter alia from BF Goodrich under the trade name Carbopol®, e.g. Carbopol 940 (molecular weight ca. 4 000 000), Carbopol 941 (molecular weight ca. 1 250 000) or Carbopol 934 (molecular weight ca. 3 000 000). They also include acrylic acid copolymers which are available for example from Rohm & Haas under the trade names Aculyn® and Acusol®, e.g. the anionic, non-associative polymers Aculyn 22, Aculyne 28, Aculyn 33 (crosslinked), Acusol 810, Acusol 823 and Acusol 830 (CAS 25852-37-3). Of specific suitability are also associative thickeners, e.g. based on modified polyurethanes (HEUR) or hydrophobically modified acrylic acid or methacrylic acid copolymers (HASE thickeners, High Alkali Swellable Emulsion).

According to one preferred embodiment, the compositions according to the invention are a skin cleaning composition.

Preferred skin cleaning compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and gels, foam baths, oil baths and scrub preparations, shaving foams, shaving lotions and shaving creams.

According to a further preferred embodiment, the compositions according to the invention are cosmetic compositions for the care and protection of the skin, nail care compositions or preparations for decorative cosmetics.

Suitable skin cosmetic compositions are e.g. face tonics, face masks, deodorants and other cosmetic lotions. Compositions for use in decorative cosmetics comprise for example concealing sticks, stage make-up, mascara and eyeshadows, lipsticks, kohl pencils, eyeliners, blushers, powders and eyebrow pencils.

Moreover, the compounds of the formula (I) and of the formula (I.1) can be used in nose strips for pore cleansing, in antiacne compositions, repellants, shaving compositions, hair removal compositions, intimate care compositions, footcare compositions and also in babycare.

The skincare compositions according to the invention are in particular W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the above-described compounds of the formula (I) and of the formula (I.1) exhibit advantageous effects. The polymers can, inter alia, contribute to the moisturization and conditioning of the skin and to improving the skin feel. By adding the polymers according to the invention, a considerable improvement in skin compatibility can be achieved in certain formulations.

Skin cosmetic and dermatological compositions preferably comprise at least one compound of the formula (I) and of the formula (I.1) in a fraction of about 0.001 to 30% by weight, preferably 0.01 to 20% by weight, very particularly preferably 0.1 to 12% by weight, based on the total weight of the composition.

Depending on the field of use, the compositions according to the invention can be applied in a form suitable for skincare, such as e.g. as cream, foam, gel, stick, mousse, milk, spray (pump spray or propellant-containing spray) or lotion.

Besides the compounds of the formula (I) and of the formula (I.1) and suitable carriers, the skin cosmetic preparations can also comprise further active ingredients and auxiliaries customary in skin cosmetics, as described above. These include preferably emulsifiers, preservatives, perfume oils, cosmetic active ingredients such as phytantriol, vitamin A, E and C, retinol, bisabolol, panthenol, photoprotective agents, bleaches, tanning agents, collagen, protein hydrolyzates, stabilizers, pH regulators, dyes, salts, thickeners, gel formers, consistency regulators, silicones, humectants, refatting agents and further customary additives.

Preferred oil and fatty components of the skin cosmetic and dermatological compositions are the aforementioned mineral and synthetic oils, such as e.g. paraffins, silicone oils and aliphatic hydrocarbons having more than 8 carbon atoms, animal and vegetable oils, such as e.g. sunflower oil, coconut oil, avocado oil, olive oil, lanolin, or waxes, fatty acids, fatty acid esters, such as e.g. triglycerides of $C_6$-$C_{30}$-fatty acids, wax esters such as e.g. jojoba oil, fatty alcohols, Vaseline, hydrogenated lanolin and acetylated lanolin, and mixtures thereof.

The polymers according to the invention can also be mixed with conventional polymers, as described above, if specific properties are to be established.

To establish certain properties such as e.g. improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyethersiloxanes or silicone resins.

The cosmetic or dermatological preparations are prepared in accordance with customary processes known to the person skilled in the art.

Preferably, the cosmetic and dermatological compositions are in the form of emulsions, in particular as water-in-oil (W/O) or oil-in-water (O/W) emulsions. However, it is also possible to select other types of formulation, for example hydrodispersions, gels, oils, oleogels, multiple emulsions, for example in the form of W/O/W or O/W/O emulsions, anhydrous ointments or ointment bases, etc.

Emulsions are prepared by known methods. Besides at least one compound of the formula (I) and of the formula (I.1), the emulsions generally comprise customary constituents, such as fatty alcohols, fatty acid esters and in particular fatty acid triglycerides, fatty acids, lanolin and derivatives thereof, natural or synthetic oils or waxes and emulsifiers in the presence of water. The selection of the emulsion-type-specific additives and the preparation of suitable emulsions is described for example in Schrader, Grundlagen and Rezepturen der Kosmetika [Fundamentals and formulations of cosmetics], Hüthig Buch Verlag, Heidelberg, 2nd edition, 1989, third section, to which reference is hereby expressly made.

A suitable emulsion, e.g. for a skin cream etc., generally comprises an aqueous phase which is emulsified by means of a suitable emulsifier system in an oil or fatty phase. For providing the aqueous phase, a compound of the general formula (I) or (I.1) can be used.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karité oil, hoplostethus oil; mineral oils, the distillation start-point of which under atmospheric pressure is ca. 250° C. and the distillation end-point of which is 410° C., such as e.g. Vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase can also comprise silicone oils that are soluble in other oils, such as dimethylpolysiloxane, methylphenylpolysiloxane and the silicone glycol copolymer, fatty acids and fatty alcohols.

It is also possible to use waxes, such as e.g. carnauba wax, candelilla wax, beeswax, microcrystalline wax, ozokerite wax and Ca, Mg and Al oleates, myristates, linoleates and stearates.

Furthermore, an emulsion according to the invention may be in the form of an O/W emulsion. An emulsion of this type usually comprises an oil phase, emulsifiers which stabilize the oil phase in the water phase and an aqueous phase, which is usually present in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bathing preparation.

Such formulations comprise at least one compound of the general formula (I) or (I.1), and also customary anionic surfactants as base surfactants and amphoteric and/or non-ionic surfactants as cosurfactants. Further suitable active ingredients and/or auxiliaries are generally selected from lipids, perfume oils, dyes, organic acids, preservatives and antioxidants, and also thickeners/gel formers, skin conditioners and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants that are customarily used in body cleaning compositions can be used in the washing, showering and bathing preparations.

Suitable surfactants are those mentioned above.

Furthermore, the shower gel/shampoo formulations can comprise additional thickeners, such as e.g. sodium chloride, PEG-55, propylene glycol oleate, PEG-120 methyl-glucose dioleate and others. Suitable commercially available further thickeners are e.g. Arlypon TT (INCI: PEG/PPG-120/10 Trimethylolpropane Trioleate (and) Laureth-2) and Arlypon F (INCI: Laureth-2). Furthermore, the shower gel/shampoo formulations can comprise preservatives, further active ingredients and auxiliaries and water.

According to a further preferred embodiment, the compositions according to the invention are a hair treatment composition.

Hair treatment compositions according to the invention preferably comprise at least one compound of the general formula (I) or (I.1) in an amount in the range from about 0.1 to 30% by weight, preferably 0.5 to 20% by weight, based on the total weight of the composition.

Preferably, the hair treatment compositions according to the invention are in the form of a setting foam, hair mousse, hair gel, shampoo, hairspray, hair foam, end fluid, neutralizer for permanent waves or hot-oil treatment. Depending on the field of application, the hair cosmetic preparations can be applied as (aerosol) spray, (aerosol) foam, gel, gel spray, cream, lotion or wax. Hairsprays comprise here both aerosol sprays and also pump sprays without propellant gas. Hair foams comprise both aerosol foams and also pump foams without propellant gas. Hairsprays and hair foams preferably comprise predominantly or exclusively water-soluble or water-dispersible components. If the compounds used in the hairsprays and hair foams according to the invention are water-dispersible, they can be applied in the form of aqueous microdispersions with particle diameters of usually 1 to 350 nm, preferably 1 to 250 nm. The solids contents of these preparations here are usually in a range from about 0.5 to 20% by weight. These microdispersions generally require no emulsifiers or surfactants for their stabilization.

In a preferred embodiment, the hair cosmetic formulations according to the invention comprise
a) 0.05 to 5% by weight, preferably 0.1 to 3% by weight, of at least one compound of the general formula (I) or (I.1),
b) 20 to 99.95% by weight of water and/or alcohol,
c) 0 to 50% by weight of at least one propellant gas,
d) 0 to 5% by weight of at least one emulsifier,
e) 0.05 to 5% by weight of at least one cosmetically active ingredient, and also
f) 0 to 20% by weight, preferably 0.1 to 10% by weight, of at least one water-soluble or water-dispersible polymer that is different from a) to e) and g),
g) 0 to 45% by weight, preferably 0.05 to 25% by weight, of further constituents,
where the components a) to g) add up to 100% by weight.

Alcohol is to be understood as meaning all alcohols customary in cosmetics, e.g. ethanol, isopropanol, n-propanol.

Further constituents are to be understood as meaning the additives customary in cosmetics, for example propellants, defoamers, interface-active compounds, i.e. surfactants, emulsifiers, foam formers and solubilizers. The interface-active compounds used may be anionic, cationic, amphoteric or neutral. Further customary constituents may also be e.g. preservatives, perfume oils, opacifiers, active ingredients, UV filters, care substances such as panthenol, collagen, vitamins, protein hydrolyzates, alpha- and beta-hydroxycarboxylic acids, stabilizers, pH regulators, dyes, viscosity regulators, gel formers, salts, humectants, refatting agents, complexing agents and further customary additives.

Furthermore, these include all styling and conditioner polymers known in cosmetics which can be used in combination with the polymers according to the invention if very specific properties are to be established.

Suitable conventional hair cosmetic polymers are for example the aforementioned cationic, anionic, neutral, non-ionic and amphoteric polymers, to which reference is hereby made.

To establish certain properties, the preparations can additionally also comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino-functional silicone compounds such as amodimethicones (CTFA).

The copolymer compositions according to the invention are particularly suitable as thickeners in hair styling preparations, in particular hair foams and hair gels.

Emulsifiers which can be used are all emulsifiers that are customarily used in hair foams. Suitable emulsifiers may be nonionic, cationic or anionic or amphoteric.

The compounds of the formula (I) and of the formula (I.1) according to the invention are also suitable for styling gels. Additional gel formers which can be used are all gel formers customary in cosmetics. In this respect, reference is made to the aforementioned conventional thickeners.

The compounds of the formula (I) and of the formula (I.1) according to the invention are also suitable for shampoo formulations which additionally comprise customary surfactants.

In the shampoo formulations, customary conditioners can be used in combination with the compounds of the formula (I) and of the formula (I.1) to achieve certain effects. These include, for example, the aforementioned cationic polymers with the name Polyquaternium according to INCI, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinyl-pyrrolidone/N-vinylimidazolium salts (Luviquat® Hold); cationic cellulose derivatives (Polyquaternium-4 and -10), acrylamide copolymers (Polyquaternium-7). Furthermore, protein hydrolyzates can be used, as can conditioning substances based on silicone compounds, for example polyalkylsiloxanes, polyarylsiloxanes, polyarylalkylsiloxanes, polyethersiloxanes or silicone resins. Further suitable silicone compounds are dimethicone cooplyols (CTFA) and amino-functional silicone compounds such as amodimethicones (CTFA). Furthermore, cationic guar derivatives such as guar hydroxypropyltrimonium chloride (INCI) can be used.

The compounds of the formula (I) and of the formula (I.1) to be used according to the invention are likewise suitable for the use for modifying rheological properties in pharmaceutical preparations of any type.

The invention further provides the use of a compound of the formula (I) or of the formula (I.1), as defined above, as auxiliary in pharmacy.

Typical pharmaceutical compositions comprise
A) at least one compound of the formula (I) or of the formula (I.1), as defined above,
B) at least one pharmaceutically acceptable active ingredient and
C) optionally at least one further pharmaceutically acceptable auxiliary different from A) and B).

Pharmaceutically acceptable auxiliaries C) are the auxiliaries that can be used as known in the field of pharmacy, food technology and related fields, in particular those listed in relevant pharmacopeia (e.g. DAB, Ph. Eur., BP, NF), as well as other auxiliaries, the properties of which do not preclude a physiological application.

Suitable auxiliaries C) may be: lubricants, wetting agents, emulsifying and suspending agents, preserving agents, antioxidants, anti-irritatives, chelating agents, emulsion stabilizers, film formers, gel formers, odor masking agents, resins, hydrocolloids, solvents, solubility promoters, neutralizing agents, permeation accelerators, pigments, quaternary ammonium compounds, refatting and superfatting agents, ointment, cream or oil base materials, silicone derivatives, stabilizers, sterilizing agents, propellants, drying agents, opacifiers, additional thickeners, waxes, emollients, white oils. An embodiment in this regard is based on expertise, as represented for example in Fiedler, H. P. Lexikon der Hilfsstoffe für Pharmazie, Kosmetik and angrenzende Gebiete [Lexicon of auxiliaries for pharmacy, cosmetics and related fields], 4th edition, Aulendorf: ECV-Editio-Kantor-Verlag, 1996.

To produce pharmaceutical compositions according to the invention, the active ingredients can be mixed or diluted with a suitable excipient. Excipients may be solid, semisolid or liquid materials, which can serve as vehicle, carrier or medium for the active ingredient. The admixing of further auxiliaries takes place if desired in the manner known to the person skilled in the art. In particular, they are aqueous solutions or solubilizates for oral or parenteral application. Furthermore, the copolymers to be used according to the invention are also suitable for use in oral administration forms such as tablets, capsules, powders, solutions. Here, they can provide the sparingly soluble medicament with an increased bioavailability. In the case of parenteral application, as well as solubilizates, it is also possible to use emulsions, for example fatty emulsions.

Pharmaceutical formulations of the aforementioned type can be obtained by processing the compounds of the formula (I) and of the formula (I.1) to be used according to the invention with pharmaceutical active ingredients according to customary methods and using known and new active ingredients.

The content of at least one compound of the general formula (I) or of the general formula (I.1) in the pharmaceutical compositions is, depending on the active ingredient, in the range from 0.01 to 50% by weight, preferably 0.1 to 40% by weight, particularly preferably 1 to 30% by weight, based on the total weight of the composition.

All pharmaceutical active ingredients and pro-drugs are suitable in principle for producing the pharmaceutical compositions according to the invention. These include benzodiazepines, antihypertensives, vitamins, cytostatics—in particular taxol, anesthetics, neuroleptics, antidepressants, antibiotics, antimycotics, fungicides, chemotherapeutics, urologics, thrombocyte platelet inhibitors, sulfonamides, spasmolytics, hormones, immunoglobulins, sera, thyroid gland therapeutics, psycho-active drugs, drugs for Parkinson's disease and other antihyperkinetics, ophthalmics, neuropathy preparations, calcium metabolism regulators, muscle relaxants, narcotics, lipid-lowering agents, liver drugs, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, circulation-promoting agents, diuretics, diagnostics, corticoids, cholinergics, bile duct therapeutics, antiasthmatics, broncholytics, beta receptor blockers, calcium antagonists, ACE inhibitors, arteriosclerosis drugs, antiphlogistics, anticoagulants, antihypotonics, antihypoglycemics, antihypertonics, antifibrinolytics, antiepileptics, antiemetics, antidotes, antidiabetics, antiarrythmics, antianemics, antiallergics, anthelmintics, analgesics, analeptics, aldosterone antagonists, slimming aids.

Examples of suitable pharmaceutical active ingredients are in particular the active ingredients specified in paragraphs 0105 to 0131 of US 2003/0157170.

Besides the application in cosmetics and in pharmacy, the compounds of the formula (I) and of the formula (I.1) to be used according to the invention are also suitable in the food sector for modifying rheological properties. The invention therefore also provides food preparations which comprise at least one of the compounds of the formula (I) and of the formula (I.1) to be used according to the invention. Within the context of the present invention, the food preparations are also to be understood as meaning nutritional supplements such as e.g. preparations containing food dyes and dietetic foods. Moreover, the specified compounds of the formula (I) and of the formula (I.1) are also suitable for modifying the rheological properties of feed additives for animal nutrition.

Moreover, the compounds of the formula (I) and of the formula (I.1) are suitable for producing aqueous preparations of nutritional supplements such as water-insoluble vitamins and provitamins such as vitamin A, vitamin A acetate, vitamin D, vitamin E, tocopherol derivatives such as tocopherol acetate and vitamin K.

In general, the compounds of the general formula (I) according to the invention can be used in all areas where a thickening effect in combination with interface-active substances is necessary.

Furthermore, the compounds of the general formula (I) are suitable for improving the solubility of other components, e.g. of other surface-active components, such as of anionic surfactants. They thus also make a positive contribution to the formation of clear surfactant-containing solutions.

The invention is illustrated in more detail by reference to the following non-limiting examples.

EXAMPLES

A) Preparation Examples

Preparation Example 1

($C_{12/14}$-Alkyl) Oligolactate (Degree of Oligomerization p=1.2)

1744.4 g (9 mol) of a $C_{12/14}$ fatty alcohol mixture (Lorol® $C_{12/14}$ spec. from BASF SE) (MW=193.82 g/mol) and 1081.0 g (10.8 mol) of lactic acid 90% (MW=90.08 g/mol) were heated to 130° C. to 150° C. in a distillation apparatus with stirring firstly under atmospheric pressure and with diminishing water separation in vacuo to 40 mbar, and water of reaction that was liberated was distilled off until an acid number of less than 5 had been reached (time ca. 8 hours). According to gas chromatographic analysis, the product had the following composition (data in area %):

| Number of lactic acid oligomers | GC area % |
|---|---|
| 0 | 7.30 |
| 1 | 67.61 |
| 2 | 17.45 |
| 3 | 3.85 |
| 4 | 0.92 |
| 5 | 0.20 |
| 6 | 0.00 |

For measurement reasons, the ascertained GC area % values do not quite add up to 100%. The small remaining residual area does not belong to any of the lactic acid oligomers.

Preparation Examples 2 to 4

In the same manner as example 1, products with the degrees of oligomerization p=2, 3 and 5 were prepared: according to gas chromatographic analysis, these products had the following compositions (data in area %):

| | Example No. | | |
|---|---|---|---|
| | 2 | 3 | 4 |
| Number of lactic acid | Degree of oligomerization p | | |
| oligomers | 2 | 3 | 5 |
| 0 | 1.48 | 0.52 | 0.53 |
| 1 | 41.11 | 21.97 | 12.99 |
| 2 | 26.91 | 21.33 | 12.65 |
| 3 | 14.31 | 16.22 | 12.58 |
| 4 | 7.33 | 11.80 | 10.69 |
| 5 | 3.60 | 8.30 | 9.18 |
| 6 | 1.71 | 5.58 | 7.29 |
| 7 | 0.79 | 3.70 | 5.77 |
| 8 | 0.33 | 2.36 | 4.33 |
| 9 | 0.07 | 1.38 | 2.91 |
| 10 | 0.00 | 0.71 | 1.67 |
| 11 | 0.00 | 0.30 | 0.82 |
| 12 | 0.00 | 0.08 | 0.30 |

Comparative Example

In the same manner as example 1, a comparison product with a degree of oligomerization p=1.08 was prepared: according to gas chromatographic analysis, this product had the following compositions (data in area %):

| Number of lactic acid oligomers | GC area % |
|---|---|
| 0 | 2.2 |
| 1 | 86.8 |
| 2 | 9 |
| 3 | 0.68 |

B) Application Examples

The thickening performance of the substances of the preparation examples according to the invention and of the comparative example was tested in various formulations. The viscosity was determined using a viscometer: Brookfield DII+pro at a measurement temperature of 22° C.

Example I

Formulation 99 g (=ca. 12% active substance) Plantapon® SF 1 g ($C_{12/14}$-alkyl) (mono/oligo)lactate (Plantapon® SF: INCI: Sodium Cocoamphoacetate and Glycerin and Lauryl Glucoside and Sodium Cocoyl Glutamate and Sodium Lauryl Glucose Carboxylate)

Plantapon® SF is based on two anionic surfactants (less than 5% sodium lauryl glucose carboxylate and less than 5% sodium cocoyl glutamate), an amphoteric surfactant (10-15% sodium cocoamphoacetate) and a nonioinc surfactant (5 to 15% lauryl glucoside) and 5 to 15% glycerol)

| | Substance from example No. | |
|---|---|---|
| | Comparative example | 1 |
| Viscosity [mPa · s]: | 1700 Spindle S 64 60 rpm | 2070 Spindle S 64 60 rpm |

Example II

Formulation 37.7 g (=ca. 10% active substance) Texapon® NSO (sodium lauryl ether sulfate with 2 mol of EO)
5.3 g (=ca. 2% active substance) Dehyton® PK 45 (cocamidopropylbetaine)
2 g NaCl
1 g ($C_{12/14}$-alkyl) (mono/oligo)lactate
Water ad 100 g

| | Example No. | | | | |
|---|---|---|---|---|---|
| | Comparative example | 1 | 2 | 3 | 4 |
| Degree of oligomerization p | 1.08 | 1.2 | 2 | 3 | 5 |
| Viscosity [mPa · s]: | 11717 Spindle S64 12 rpm | 21445 Spindle S64 12 rpm | 25645 Spindle S64 12 rpm | 28844 Spindle S64 12 rpm | 22795 Spindle S64 12 rpm |

Example III

Formulation 99 g (=ca. 12% active substance) Plantapon® SF
1 g ($C_{12/14}$-alkyl) (mono/oligo)lactate
Measurement temperature T=23° C.

| | Example No. | | | |
|---|---|---|---|---|
| | 1 | 2 | 3 | 4 |
| Degree of oligomerization p | 1.2 | 2 | 3 | 5 |
| Viscosity [mPa · s]: | 1218 Spindle TC 93 50 rpm | 1626 Spindle TC 93 20 rpm | 7092 Spindle TC 93 6 rpm | 798 Spindle TC 93 60 rpm |

The invention claimed is:

1. A composition comprising a mixture of compounds of the general formula (I):

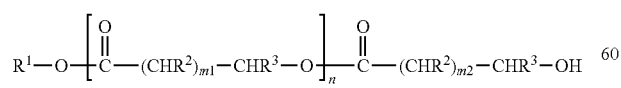
(I)

wherein:

$R^1$ is hydrogen or a linear or branched aliphatic hydrocarbon radical having 1 to 30 carbon atoms and 0, 1, 2 or 3 double bonds, $R^2$, independently of one another, are selected from hydrogen, methyl, ethyl, —OH, —COOR$^4$, —CH$_2$—OH and —CH$_2$—COOR$^4$, where the radicals R$^4$ are hydrogen or a linear or branched aliphatic hydrocarbon radical having 1 to 30 carbon atoms and 0, 1, 2 or 3 double bonds, $R^3$, independently of one another, are selected from hydrogen, methyl, ethyl, —OH, —COOR$^5$, —CH$_2$—OH and —CH$_2$—COOR$^5$, where the radicals R$^5$ are hydrogen or a linear or branched aliphatic hydrocarbon radical having 1 to 30 carbon atoms and 0, 1, 2 or 3 double bonds, n is on average a value from 0.1 to 100, m1 and m2, independently of one another, are 0 or 1, wherein the compounds of general formula (I) have an average degree of oligomerization (p) of n+1, and wherein the compounds of the general formula (I) differ in the degree of oligomerization, with the proviso that at least one of the radicals $R^1$, $R^4$ or $R^5$ is a linear or branched aliphatic hydrocarbon radical having 6 to 30 carbon atoms and 0, 1, 2 or 3 double bonds obtained by a process in which at least one hydroxycarboxylic acid of the general formula (I.A)

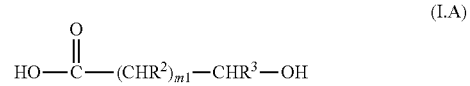
(I.A)

in which $R^2$, independently of one another, are selected from hydrogen, methyl, ethyl, —OH, —COOR$^4$, —CH$_2$—OH and —CH$_2$—COOR$^4$, where the radicals R$^4$ are hydrogen or a linear or branched aliphatic hydrocarbon radical having 1 to 30 carbon atoms and 0, 1, 2 or 3 double bonds, $R^3$, independently of one another, are selected from hydrogen, methyl, ethyl, —OH, —COOR$^5$, —CH$_2$—OH and —CH$_2$—COOR$^5$, where the radicals R$^5$ are hydrogen or a linear or branched aliphatic hydrocarbon radical having 1 to 30 carbon atoms and 0, 1, 2 or 3 double bonds, m1 is 0 or 1, is reacted in an esterification reaction, where the esterification takes place in the presence of at least one alcohol R$^1$—OH, where R$^1$ is hydrogen or a linear or branched aliphatic hydrocarbon radical having 1 to 30 carbon atoms and 0, 1, 2 or 3 double bonds, or the product of the esterification of the hydroxycarboxylic acid(s) (I.A) is then reacted with at least one alcohol R1-OH.

2. The composition according to claim 1, wherein m1 and m2 have the same meaning.

3. The composition according to claim 1, wherein the mixture of compounds of the general formula (I) is derived from lactic acid, glycolic acid, malic acid, tartaric acid or mixtures thereof.

4. The composition according to claim 1, wherein the mixture of compounds of the general formula (I) is selected from compounds of the formula (I.1):

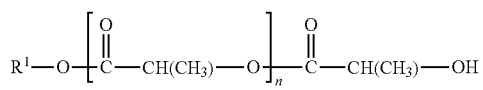

(I.1)

wherein:

R$^1$ is a linear or branched hydrocarbon radical having 6 to 30 carbon atoms and 0, 1, 2 or 3 double bonds, and n is on average a value of from 0.1 to 100.

5. The composition according to claim 1, wherein n is a value from 0.15 to 50.

6. The composition according to claim 1, wherein at least one of the radicals R$^1$, R$^4$ and R$^5$ is n-hexyl, 2-ethylhexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, and combinations thereof.

7. The composition according to claim 1, wherein at least one of the radicals R$^1$, R$^4$ and R$^5$ is derived from linear saturated alcohols having 8 to 18 carbon atoms.

8. The composition according to claim 1, wherein at least one of the radicals R$^1$, R$^4$ and R$^5$ is derived from a mixture of linear saturated C$_{12}$-/C$_{14}$-alcohols.

9. A process for preparing the composition of claim 1 comprising a mixture of compounds having the general formula (I):

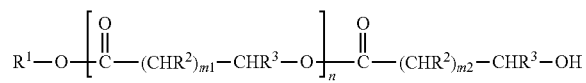

(I)

the process comprising:

reacting at least one hydroxycarboxylic acid of the general formula (I.A):

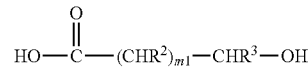

(I.A)

in an esterification reaction, where the esterification takes place in the presence of at least one alcohol R$^1$—OH or the product of the esterification of the hydroxycarboxylic acid(s) (I.A) is then reacted with at least one alcohol R$^1$—OH, wherein R$^1$ is hydrogen or a linear or branched aliphatic hydrocarbon radical having 1 to 30 carbon atoms and 0, 1, 2 or 3 double bonds, the radicals R$^2$, independently of one another, are selected from hydrogen, methyl, ethyl, —OH, —COOR$^4$, —CH$_2$—OH and —CH$_2$—COOR$^4$, where the radicals R$^4$ are hydrogen or a linear or branched aliphatic hydrocarbon radical having 1 to 30 carbon atoms and 0, 1, 2 or 3 double bonds, the radicals R$^3$, independently of one another, are selected from hydrogen, methyl, ethyl, —OH, —COOR$^5$, —CH$_2$—OH and —CH$_2$—COOR$^5$, where the radicals R$^5$ are hydrogen or a linear or branched aliphatic hydrocarbon radical having 1 to 30 carbon atoms and 0, 1, 2 or 3 double bonds, n is on average a value from 0.1 to 100, m1 and m2, independently of one another, are 0 or 1, with the proviso that at least one of the radicals R$^1$, R$^4$ or R$^5$ is a linear or branched aliphatic hydrocarbon radical having 6 to 30 carbon atoms and 0, 1, 2 or 3 double bonds.

10. A cosmetic or pharmaceutical composition comprising:

a) the composition comprising the mixture of compounds of the general formula (I) according to claim 1, b) at least one cosmetically or pharmaceutically acceptable active ingredient, and c) optionally at least one cosmetically or pharmaceutically acceptable auxiliary different from the components a) and b).

11. The composition comprising the mixture of compounds of the general formula (I) according to claim 1, which is effective as a thickener for aqueous surfactant-containing compositions.

12. The composition comprising the mixture of compounds of the general formula (I) according to claim 1, which is effective as a component for the formulation of one or more of:

cosmetic compositions,
pharmaceutical compositions,
detergents and cleaners,
crop protection compositions,
wetting agents, and
paints, coatings, adhesives, leather-treatment or textile-treatment compositions.

13. The composition according to claim 5, wherein n is a value from 0.2 to 20.

* * * * *